(12) United States Patent
Lightcap et al.

(10) Patent No.: US 8,996,169 B2
(45) Date of Patent: Mar. 31, 2015

(54) NEURAL MONITOR-BASED DYNAMIC HAPTICS

(75) Inventors: Chris Alan Lightcap, Davie, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 624 days.

(21) Appl. No.: 13/339,541

(22) Filed: Dec. 29, 2011

(65) Prior Publication Data

US 2013/0172902 A1  Jul. 4, 2013

(51) Int. Cl.
*A61B 19/00* (2006.01)
*A61B 18/00* (2006.01)

(52) U.S. Cl.
CPC ............. *A61B 19/2203* (2013.01); *A61B 19/30* (2013.01); *A61B 2018/00339* (2013.01); *A61B 2018/0044* (2013.01); *A61B 2018/00839* (2013.01); *A61B 2019/2292* (2013.01); *Y10S 901/02* (2013.01); *Y10S 901/34* (2013.01); *Y10S 901/35* (2013.01)
USPC ........... 700/250; 700/245; 700/255; 700/258; 700/260; 700/261; 901/2; 901/34; 901/35; 600/554

(58) Field of Classification Search
CPC ............... A61B 19/2203; A61B 19/50; A61B 19/5244; A61B 2019/2203; A61B 2019/2219; A61B 2019/2223; A61B 2019/223; A61B 2019/2292; A61B 2019/501–2019/508; A61B 2019/481; A61B 5/04001–5/0496; A61B 5/4893; G05B 2219/36432; G05B 2219/36435; G05B 2219/45119; G05B 2219/45123; B25J 9/1633; G06F 3/015; G06F 3/016
USPC ......... 700/245, 250, 253, 255, 258, 260, 261; 600/554; 74/490.01; 901/2, 34, 35, 50
See application file for complete search history.

(56) References Cited

U.S. PATENT DOCUMENTS

| | | | |
|---|---|---|---|
| 7,717,932 B2 | 5/2010 | McFarlin et al. | |
| 8,010,180 B2 | 8/2011 | Quaid et al. | |
| 2004/0128026 A1* | 7/2004 | Harris et al. | 700/245 |
| 2007/0239187 A1 | 10/2007 | Brunnett et al. | |
| 2008/0010705 A1* | 1/2008 | Quaid et al. | 901/8 |
| 2010/0170362 A1 | 7/2010 | Bennett et al. | |
| 2010/0198219 A1* | 8/2010 | McFarlin et al. | 606/45 |
| 2011/0270120 A1 | 11/2011 | McFarlin et al. | |

* cited by examiner

*Primary Examiner* — Spencer Patton
(74) *Attorney, Agent, or Firm* — Foley & Lardner LLP

(57) ABSTRACT

A computer-assisted surgery system may have a robotic arm including a surgical tool and a processor communicatively connected to the robotic arm. The processor may be configured to receive, from a neural monitor, a signal indicative of a distance between the surgical tool and a portion of a patient's anatomy including nervous tissue. The processor may be further configured to generate a command for altering a degree to which the robotic arm resists movement based on the signal received from the neural monitor; and send the command to the robotic arm.

21 Claims, 9 Drawing Sheets

NEURAL MONITOR-BASED DYNAMIC HAPTICS

TECHNICAL FIELD

The present disclosure relates generally to surgical systems and, more particularly, to dynamically altering the haptic response of a surgical system based on output from a neural monitor.

BACKGROUND

Many surgical procedures depend on accurate drilling or resection of portions of a patient's bone. For example, in various spinal surgeries, a surgeon may be required to drill one or more holes in a patient's spine. However, if the surgeon drills a hole improperly, e.g., too deeply, at an incorrect trajectory or angle, etc., the surgeon may cause irreparable damage to the patient. For instance, a surgeon may be required to drill one or more pilot holes for pedicle screws to be inserted in the patient's spine. If the surgeon drills the pilot holes incorrectly, the surgeon may cause damage to the spinal cord, thereby injuring the patient.

In some surgeries, a surgeon may use a computer-assisted surgery system when drilling or resecting portions of the patient's bone. Moreover, the computer-assisted surgery system may include a haptic feedback system to constrain or inhibit the surgeon from manually moving the surgical tool beyond predefined virtual boundaries defined by haptic objects. The virtual boundaries may be established to prevent the surgeon from undesired interactions with a patient's anatomy. For example, the haptic boundaries may help to prevent the surgeon from improperly drilling or resecting the patient's bone.

However, a variety of factors such as inaccurately or improperly defined haptic boundaries, improper registration of the patient's bone to the computer-assisted surgery system, etc., may affect the accuracy of the computer-assisted surgery system. In some surgeries, such as various spinal surgeries, inaccuracies may lead to undesired interaction with the spinal cord or other nerves and injure the patient. Moreover, in some instances, such interaction may have disastrous consequences, such as full or partial paralysis, nerve damage, etc.

Patient monitoring systems are known that may be used to monitor electromyographic (EMG) activity of a patient to determine the proximity of a cutting tool or other instrument to a patient's nerve. For example, an electrical potential may be applied to the cutting tool, and EMG signals may be read from sensors placed in muscles or other tissue innervated by the nerves of concern. By comparing the electrical signal applied to the cutting tool with the signals from the sensors, the patient monitoring system may determine the distance between the cutting tool and a nerve. Moreover, certain systems may disable power to the cutting tool based on the determined distance.

However, enabling and disabling power to a cutting tool may adversely affect the quality and accuracy of the resection or drilling being performed, especially if the cutting tool continuously toggles between an enabled and disabled state. Moreover, it may be difficult to determine an acceptable threshold distance for disabling power to the cutting tool.

The presently disclosed systems and methods for neural monitor-based dynamic haptics are directed to overcoming one or more of the problems set forth above and/or other problems in the art.

SUMMARY

According to one aspect, the present disclosure is directed to a computer-implemented method for controlling a surgical system. The method may include receiving, from a neural monitor, a signal indicative of a distance between a surgical tool connected to a robotic arm and a portion of a patient's anatomy including nervous tissue. A command may be generated for altering a degree to which the robotic arm resists movement based on the signal received from the neural monitor.

According to another aspect, the present disclosure is directed to a computer-assisted surgery system. The system may include a robotic arm, including a surgical tool, and a processor. The processor may be communicatively connected to the robotic arm and configured to receive, from a neural monitor, a signal indicative of a distance between the surgical tool and a portion of a patient's anatomy including nervous tissue. The processor may be further configured to generate a command for altering a degree to which the robotic arm resists movement based on the signal received from the neural monitor; and send the command to the robotic arm.

According to yet another aspect, the present disclosure is directed to a computer-implemented method for controlling a surgical system. The method may include receiving, at a processor associated with a computer, a signal from a neural monitor indicative of a distance between a surgical tool connected to a robotic arm and a portion of a patient's anatomy including nervous tissue. The method may also include determining, by the processor, a haptic feedback command based on the signal received from the neural monitor.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

Figure 1:
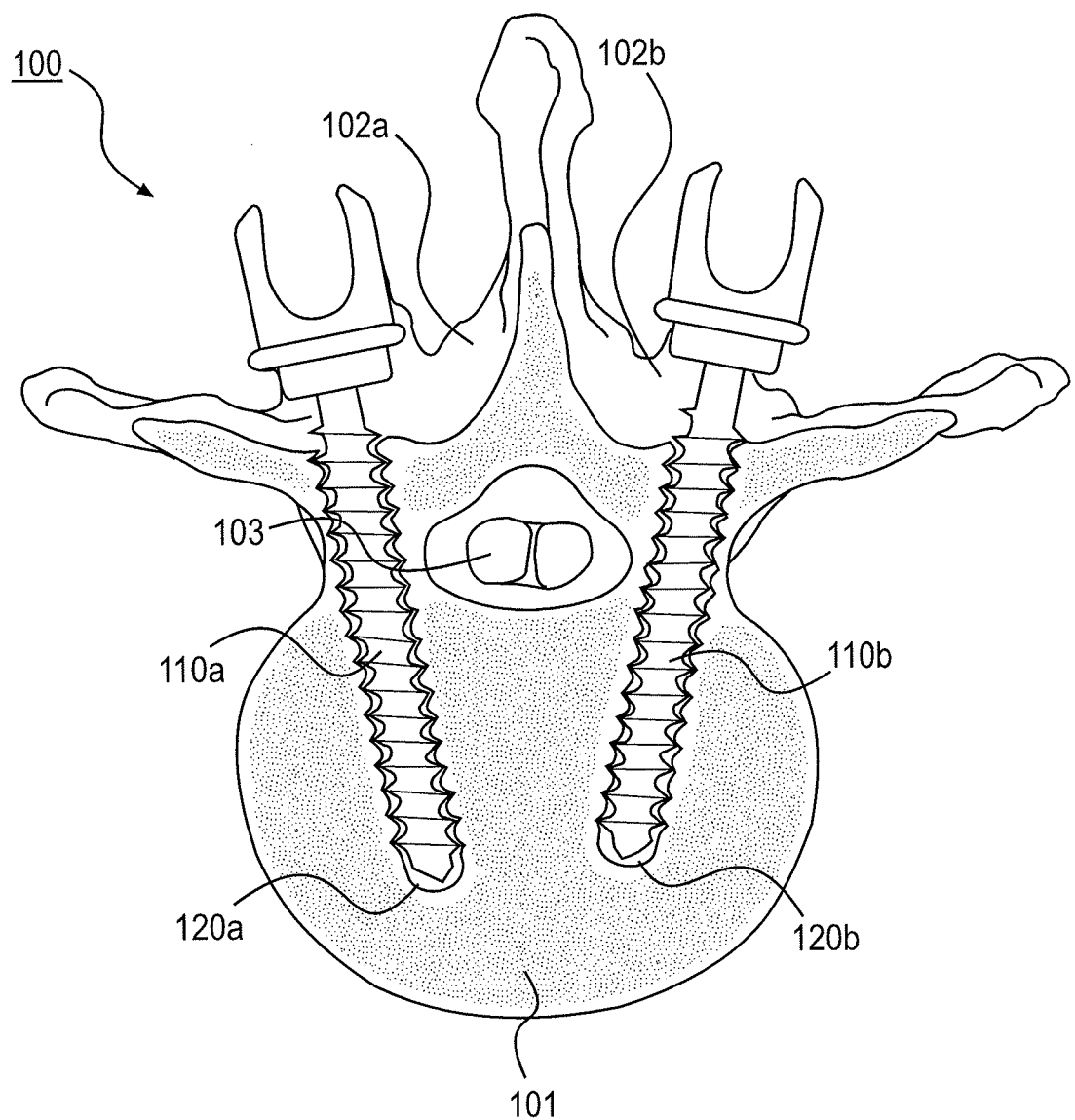
FIG. 1 is an illustration of a surgical environment, consistent with disclosed embodiments.

FIG. 1 illustrates an exemplary surgical environment, consistent with disclosed embodiments. For example, FIG. 1 shows a cross-sectional view of a vertebra 100. During surgery, such as spinal fusion surgery, a surgeon may insert one or more of pedicle screws 110a and 110b through pedicle regions 102a and 102b, respectively, and into vertebral body 101 of vertebra 100. Prior to inserting pedicle screws 110a and 110b, the surgeon may drill or otherwise cut pilot holes 120a and 120b corresponding to pedicle screws 110a and 110b. The pilot holes may facilitate insertion of pedicle screws 110a and 110b into vertebra 100.

As shown in FIG. 1, pedicle screws 110a and 110b may be inserted in close proximity to spinal cord 103, and thus, the placement of pedicle screws 110a and 110b and their corresponding pilot holes must be precisely aligned so as to avoid interacting with or damaging spinal cord 103. If a surgeon drills pilot holes 120a or 120b at an improper angle and/or too deeply, pedicle screws 110a or 110b or the cutting tool used to drill pilot holes 120a and 120b may damage spinal cord 103.

Exemplary embodiments of the present disclosure, discussed in greater detail below, may reduce the risk of injury to spinal cord 103, e.g., by detecting one or more electromyographic (EMG) signals to measure a distance between the cutting tool used to drill pilot holes 120a and 120b and dynamically altering a degree to which a robotic arm connected to the cutting tool resists movement based on the measured distance. This way, if a surgeon operates a cutting tool in dangerous proximity to spinal cord 103, the surgeon may experience haptic feedback from the robotic arm, preventing the surgeon from moving the cutting tool closer to spinal cord 103.

Moreover, as discussed above, FIG. 1 represents an exemplary surgical environment in which embodiments of the present disclosure may be used. For example, disclosed embodiments may be used in spinal surgeries other than spinal fusion, such as dynamic stabilization surgeries, discectomies, foramenotomies, laminectomies, etc. Further, disclosed embodiments may be used in any surgery in which a surgeon may drill, resect, or modify any portion of the patient's anatomy in proximity to spinal cord 103, a nerve or group of nerves, or any other portion of the patient's anatomy including nervous tissue. For example, disclosed embodiments may also be used in surgeries performed in proximity to the facial nerve, such as mastoidectomies or other otolaryngolocial surgeries. EMG signals may be used to measure the distance between a cutting tool and the facial nerve, in accordance with disclosed embodiments.

Figure 2:
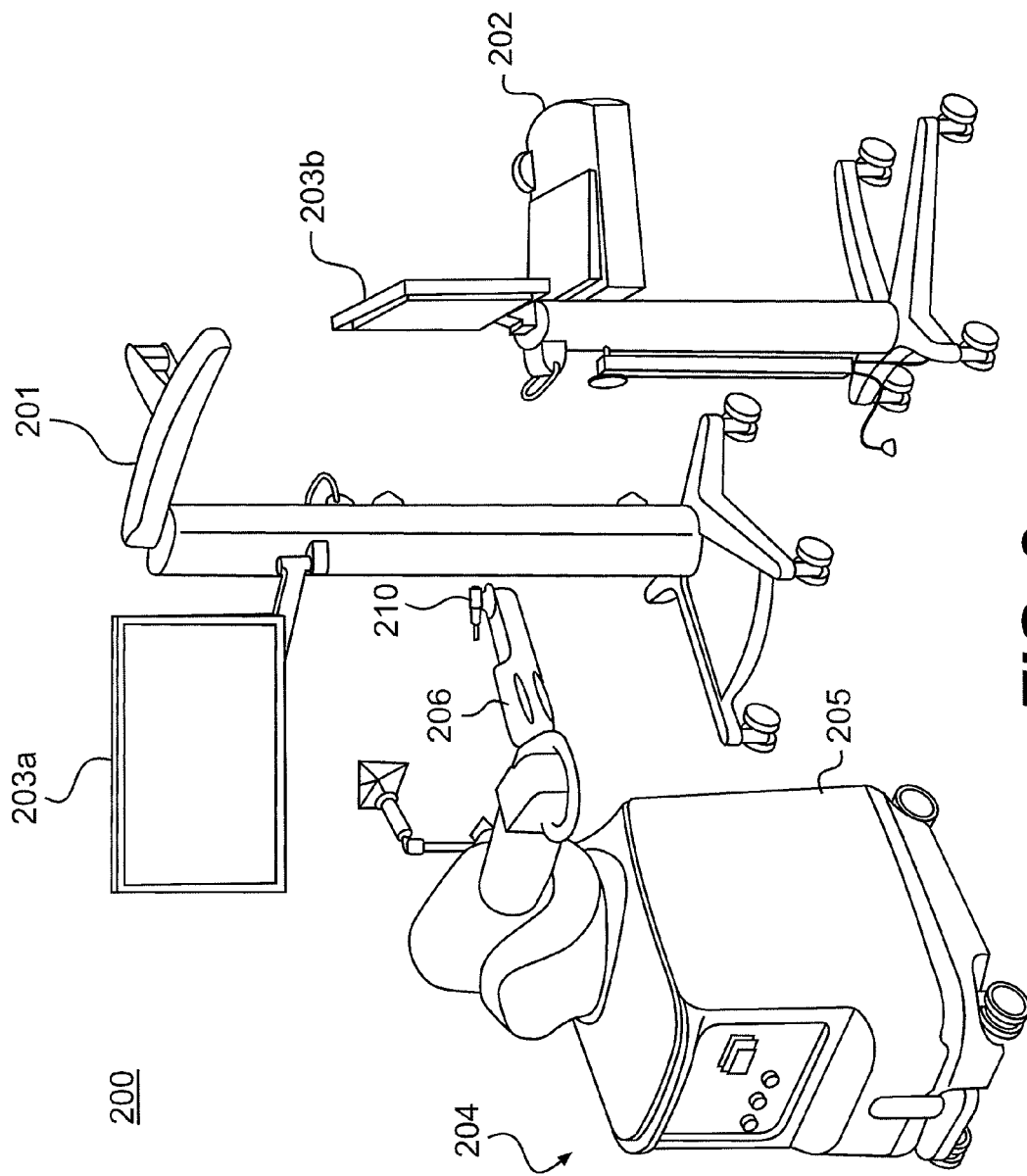
FIG. 2 is an illustration of an exemplary computer-assisted surgery (CAS) system, in which certain methods consistent with the disclosed embodiments may be implemented, consistent with disclosed embodiments.

FIG. 2 illustrates an exemplary computer-assisted surgery (CAS) system 200, in which processes and features associated with certain disclosed embodiments may be implemented. CAS system 200 may be configured to perform a wide variety of surgical procedures, including spinal surgeries such as spinal fusion and dynamic stabilization surgeries, discectomies, foramenotomies, and laminectomies. As illustrated in FIG. 2, CAS system 200 may comprise a tracking system 201, a computer-assisted navigation system 202, one or more display devices 203a, 203b, and a robotic arm 204. It should be appreciated that CAS system 200, as well as the methods and processes described herein, may be applicable to many different types of surgical procedures. Although certain disclosed embodiments may be described with respect to drilling pedicle screw pilot holes for spinal fusion techniques and other operations performed during spinal surgeries, those skilled in the art will appreciate that the concepts and methods described herein may be applicable to other types of surgeries. For example, concepts and methods described herein may be applicable to other procedures where portions of a patient's anatomy may be drilled, resected, or otherwise modified by CAS system 200.

Robotic arm 204 can be used in an interactive manner by a surgeon to perform a surgical procedure, such as a spinal surgery, on a patient. As shown in FIG. 2, robotic arm 204 includes a base 205, an articulated arm 206, a force system (not shown), and a controller (not shown). Articulated arm 206 may include one or more joints about which articulated arm 206 may be pivoted, rotated, or otherwise moved. A surgical tool 210 (e.g., an end effector having an operating member, such as a saw, reamer, burr, drill, etc.) may be coupled to the articulated arm 206. The surgeon can manipulate surgical tool 210 by grasping and manually moving articulated arm 206 and/or surgical tool 210.

The force system and controller are configured to provide control or guidance to the surgeon during manipulation of the surgical tool. The force system is configured to provide at least some force to the surgical tool via articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale, Fla. The force system and controller may be housed within robotic arm 204. Moreover, in certain embodiments, all or part of the force system may be housed within another component of CAS system 200, such as computer-assisted navigation system 202, for example.

Tracking system 201 may include any suitable device or system configured to track the relative locations, positions, orientations, and/or poses of the surgical tool 210 (coupled to robotic arm 204) and/or positions of registered portions of a patient's anatomy, such as bones. Such devices may employ optical, mechanical, or electromagnetic pose tracking technologies. According to one embodiment, tracking system 201 may comprise a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during the surgical procedure, navigation system 202 may display images related to the surgical procedure on one or both of the display devices 203a, 203b.

Figure 3:
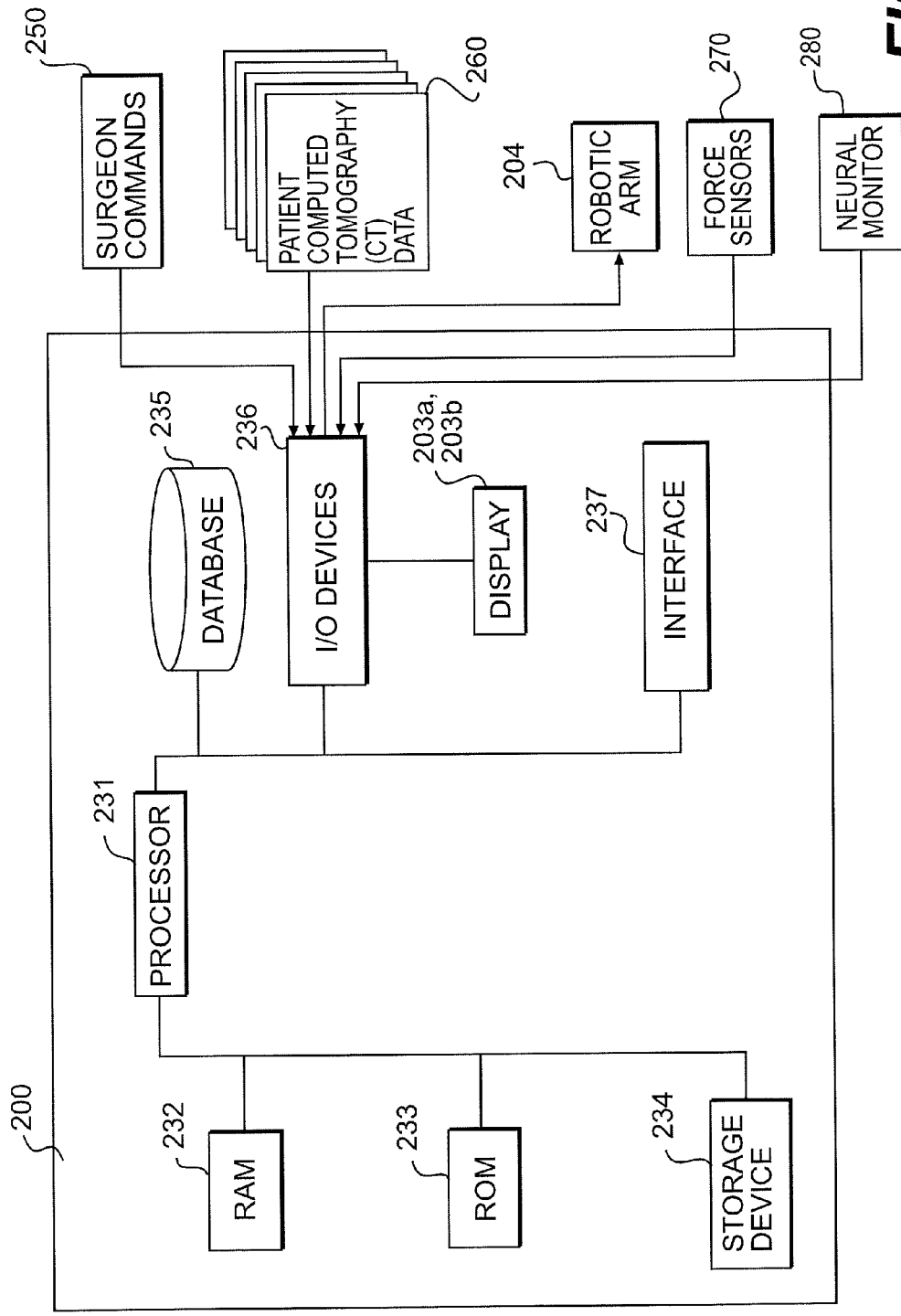
FIG. 3 is a schematic diagram of an exemplary computer system, which may be used in one or more components associated with the CAS system illustrated in FIG. 2.

One or more constituent components of CAS system 200, such as navigation system 202 and/or robotic arm 204, may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as tracking software, surgical navigation software, 3-D bone modeling or imaging software, software for establishing virtual haptic boundaries for use with the force system of robotic arm 204 to provide haptic feedback to surgical tool 210, and/or software for providing dynamic haptic feedback to a surgeon based on a measured distance between surgical tool 210 and a portion of the patient's anatomy, such as spinal cord 103. CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 3, processor 231 may be communicatively coupled to RAM 232, ROM 233, storage device 234, database 235, I/O devices 236, and network interface 237. Processor 231 may be configured to execute sequences of computer program instructions to perform various processes, described in greater detail below. The computer program instructions may be loaded into RAM 232 for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202 and/or robotic arm 204, to perform functions or tasks associated with CAS system 200. For example, computer readable media may include instructions for causing the CAS system 200 to perform one or more methods for dynamically altering a degree to which robotic arm 204 (e.g., articulated arm 206) resists movement based on a distance between surgical tool 210 and a portion of the patient's anatomy, such as spinal cord 103, that may be measured by a neural monitor, for example. In certain embodiments, the instructions may cause CAS system 200 to alter the degree to which robotic arm 204 resists movement by generating a damping torque based on the distance measured by the neural monitor. In other embodiments, the instructions may cause CAS system 200 to alter the degree to which robotic arm 204 resists movement by modifying an amount of force feedback being applied to robotic arm 204 based on the measured distance. In still other embodiments, the instructions may cause CAS system 200 to alter the degree to which robotic arm 204 resists movement by directly modifying a haptic object impedance value or haptic object admittance value based on the measured distance.

Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203a, 203b, including a graphical user interface (GUI) for outputting information on a monitor. I/O devices 236 may also include peripheral devices such as, for example, a printer for printing information associated with CAS system 236, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., bones) in software.

I/O devices 236 may also include one or more components configured to receive information about CAS system 200 and/or information related to a patient undergoing surgery. For example, I/O devices 236 may include one or more force sensors 270. Force sensors 270 may be configured to detect a force being applied to surgical tool 210 and/or articulated arm 206 of robotic arm 204 by the surgeon. Moreover, other sensors (not shown) may also be included that measure, e.g., a position, velocity, and/or acceleration of surgical tool 210 and/or articulated arm 206 and send this information to processor 231. Moreover, I/O devices 236 may include a neural monitor 280 which, as discussed in greater detail below, may generate and send a signal indicative of a distance between surgical tool 210 and a portion of a patient's anatomy including nervous tissue, such as spinal cord 103, for example.

Processor 231 may be configured to establish virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site. During surgery, processor 231 may send haptic feedback commands to robotic arm 204 based on the virtual haptic geometry. For example, processor 231 may determine a distance between surgical tool 210 and one or more virtual representations, and may generate haptic feedback commands based on the distance.

Processor 231 may also generate haptic feedback commands based on a measured distance between surgical tool 210 and a portion of a patient's anatomy, such as spinal cord 103. The distance may be measured, e.g., by neural monitor 280. In certain embodiments, the haptic feedback commands generated based on the distance measured by neural monitor 280 may be combined with the haptic feedback commands generated based on the distance from the virtual representations of the patient's anatomy, such that the haptic feedback command provided to robotic arm 204 is a combination of the two haptic feedback commands.

Figure 4:
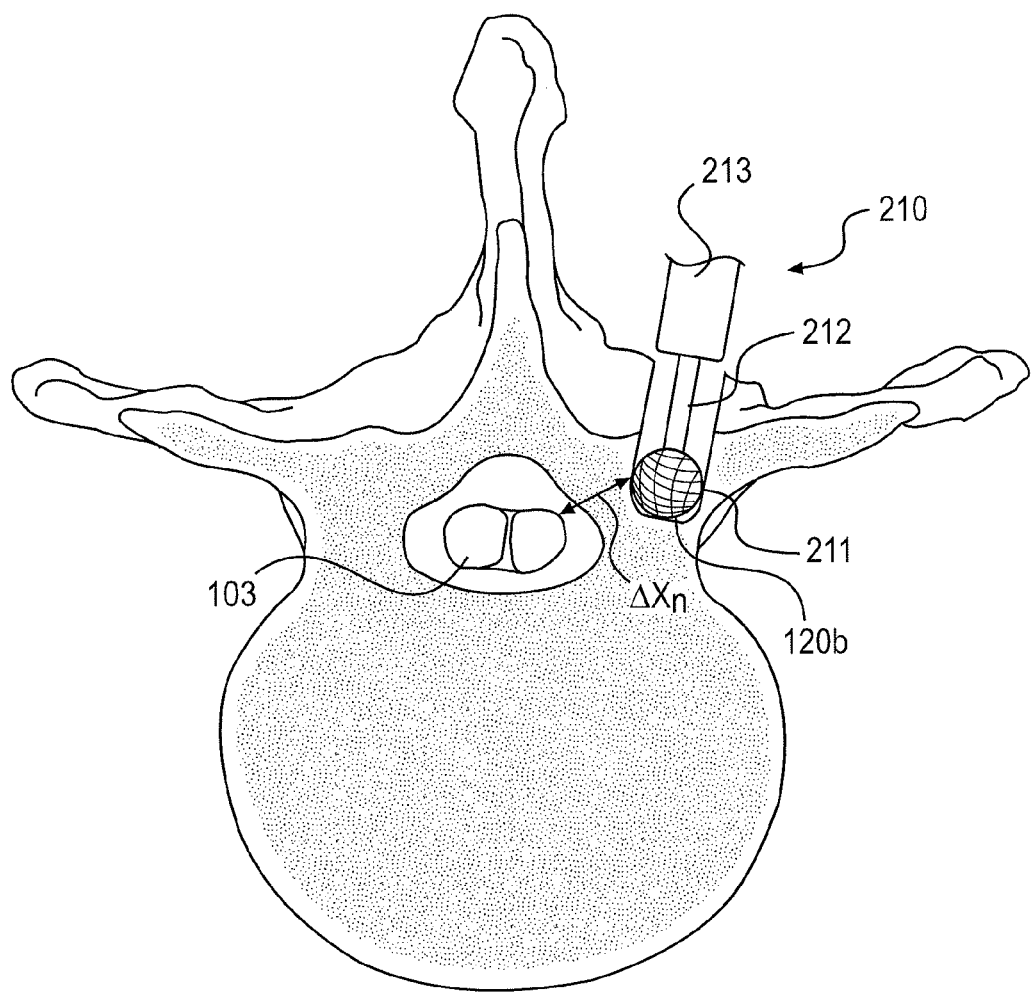
FIG. 4 is another illustration of a surgical environment, consistent with disclosed embodiments.

FIG. 4 is another illustration of a surgical environment, according to exemplary embodiments. In FIG. 4, a surgeon may begin to drill pilot hole 120b with surgical tool 210. At distal end 211, surgical tool 210 may include, e.g., a drill bit, burr, etc., to perform drilling, resection, or any other modification of the patient's anatomy. In exemplary embodiments, an electrical current may be applied to distal end 211. The electrical current may be applied to distal end 211 through shaft 212 via a wire (not shown) electrically connected to shaft 212 through a conductive bearing (not shown) lubricated with conductive grease. The electrical current may be generated, e.g., by neural monitor 280. In other embodiments, the electrical current may be applied to shaft 212 using a conductive brush in contact with shaft 212, similar to a motor commutation system. Moreover, those skilled in the art will appreciate that an electrical current may be applied to distal end 211 via any other means consistent with disclosed embodiments. In certain embodiments, surgical tool 210 may include a non-conductive sleeve 213 to electrically isolate the electrical signal and prevent the user (e.g., a surgeon) from interacting with the signal.

As the surgeon operates surgical tool 210, e.g., to drill pilot hole 120b, the electrical signal applied to distal end 211 may be used by neural monitor 280 to determine a distance, $\Delta x_n$, between distal end 211 and spinal cord 103. For example, in addition to generating the electrical signal, neural monitor 280 may also include one or more sensors or probes located at or around spinal cord 103 and/or in or around muscles innervated by spinal cord 103. Neural monitor 280 may also include a reference sensor or probe in a location separated from spinal cord 103, e.g., on the patient's forehead. Neural monitor 280 may monitor the incoming signals received at these sensors or probes, and may compare the incoming signals to the electrical signal being applied to distal end 211. Based on this comparison, neural monitor 280 may determine a distance between distal end 211 (e.g., the cutting tip of surgical tool 210) and spinal cord 103. While spinal cord 103 is used in the embodiment discussed above, those skilled in the art will appreciate that a distance to any nerve or group of nerves may be determined by neural monitor 280 using similar techniques.

Neural monitor 280 may send signals to CAS system 200 that are indicative of the determined distance between distal end 211 (e.g., the cutting tip of surgical tool 210) and spinal cord 103. CAS system 200 may then dynamically vary the degree to which robotic arm 204 resists movement based on these signals. For example, processor 231 may receive the signals indicating the distance between distal end 211 and spinal cord 103, and, based on these signals, may generate and send one or more commands to robotic arm 204 such that a user operating articulating arm 206 or surgical tool 210 of robotic arm 204 experiences haptic feedback based on the distance between distal end 211 and spinal cord 103, as determined by neural monitor 280. In certain embodiments, the user may experience haptic feedback such that robotic arm 204 becomes more difficult to move as distal end 211 moves closer to spinal cord 103.

FIGS. 5-8, discussed in greater detail below, illustrate exemplary embodiments of how CAS system 200 may dynamically vary the degree to which robotic arm 204 resists movement based on the signals received from neural monitor 280. Those skilled in the art will appreciate that the system control diagrams shown in FIGS. 5-8 may be implemented by processor 231, for example, based on software stored in one or more of RAM 232, ROM 233, and storage device 234.

Figure 5:
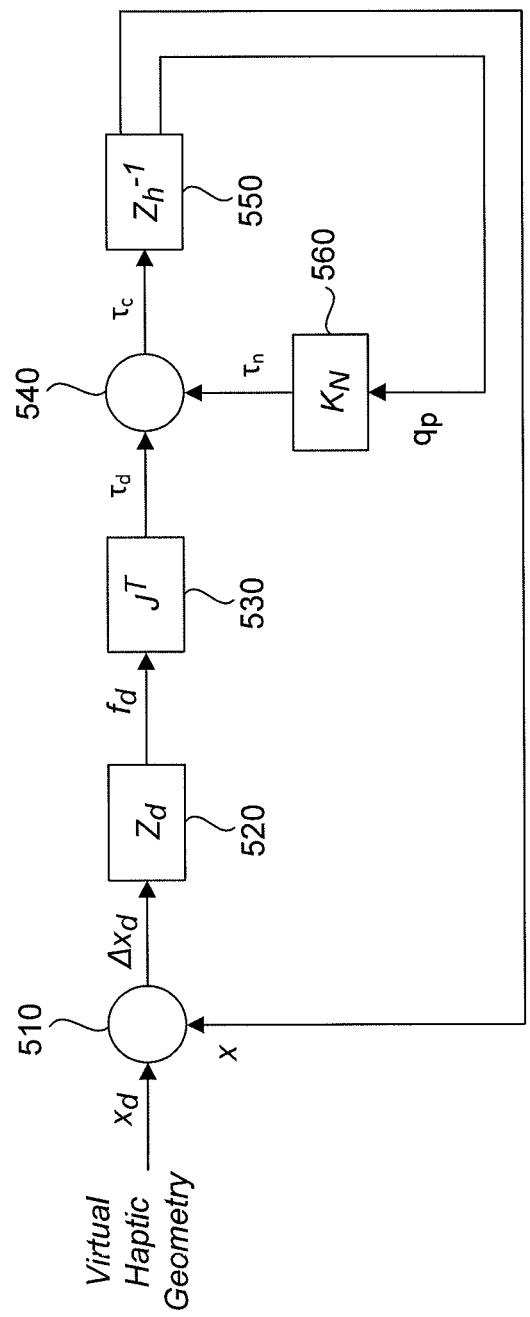
FIG. 5 is a block diagram of an exemplary control system which may be employed by the CAS system illustrated in FIG. 2.

FIG. 5 shows a system control diagram in accordance with an exemplary embodiment in which processor 231 may control robotic arm 204 by means of impedance control. For example, in FIG. 5, processor 231 may alter an impedance of robotic arm 204 based on a virtual damping torque $\tau_n$ generated in accordance with the distance between distal end 211 of surgical tool 210 and spinal cord 103, as measured by neural monitor 280. The virtual damping torque $\tau_n$ may be combined with a torque $\tau_d$ that is generated based on the virtual haptic geometry used to model the patient's anatomy or any other object associated with the surgical environment. This combined torque $\tau_c$ may then be used to generate a haptic feedback command that may be sent to the force system of robotic arm 204. Robotic arm 204 may use the haptic feedback command to control actuators therein so as to vary the impedance of robotic arm 204 based on the command.

For example, in FIG. 5, processor 231 may receive a desired position $x_d$ and an actual position x of surgical tool 210. Desired position $x_d$ and actual position x may include a point or set of points in three-dimensional space to represent their respective positions. Desired position $x_d$ may be determined based on the virtual haptic geometry used to model the patient's anatomy and/or objects associated with the surgical environment. For example, desired position $x_d$ may be a point or set of points located at the edge of a virtual boundary created based on one or more of the haptic objects. The actual position x of surgical tool 210 may be detected by tracking system 201 or by one or more position sensors configured to measure angular positions of one or more joints in robotic arm 204, for example.

Processor 231 may calculate a difference $\Delta x_d$ between the desired position and the actual position of surgical tool 210 (block 510). Processor 231 may then calculate a haptic object force $f_d$ based on difference $\Delta x_d$ (block 520). For example, processor 231 may calculate $f_d$ by multiplying difference $\Delta x_d$ by a haptic object impedance value $Z_d$. In certain embodiments, haptic object impedance value $Z_d$ may be a fixed value for the haptic object to which it corresponds, e.g., haptic object impedance value $Z_d$ may be 3,000 N/m for a particular haptic object. In other embodiments, discussed in greater detail below, haptic object impedance value $Z_d$ may be variable.

In certain embodiments, haptic object impedance value $Z_d$ may include an inertia component M, a damping component B, and a stiffness component K. In this embodiment, processor 231 may also determine a first derivative and/or a second derivative of the difference values $\Delta x_d$, and may calculate haptic object force $f_d$ based on the impedance components M, B, and/or K as well as $\Delta x_d$ and its first and/or second derivatives. For example, processor 231 may determine $f_d$ in accordance with the following equation:

$$f_d = M(\Delta \ddot{x}_d) + B(\Delta \dot{x}_d) + K(\Delta x_d), \quad (1)$$

where M, B, and K are each constant values. In one embodiment, M may be equal to zero, such that $f_d$ is determined based on a damping component B and a stiffness component K. Of course, in other embodiments, any combination of M, B, and K may be zero, such that $f_d$ is determined based on the remaining non-zero components.

After calculating haptic object force $f_d$, processor 231 may calculate a haptic object torque $\tau_d$ to be applied to robotic arm 204, e.g. by one or more actuators at corresponding joints of robotic arm 204 (block 530). Thus, at block 530, processor 231 may utilize the Jacobian transpose to determine a haptic object torque $\tau_d$ that will generate a force at articulated arm 206 equal to haptic object force $f_d$.

In certain embodiments, neural monitor torque $\tau_n$ may embody a virtual damping torque. For example, processor 231 may calculate neural monitor torque $\tau_n$ at block 560 as $\tau_n = -K_N * q_p$, where $q_p$ represents the joint angular velocity of one or more joints of robotic arm 204 and $K_N$ represents the neural monitor gain. Joint angular velocity $q_p$ may be measured, e.g., by one or more sensors at robotic arm 204. Neural monitor gain $K_N$ may be variable based on the distance between surgical tool 210 and a portion of the patient's anatomy, such as spinal cord 103, as measured by neural monitor 280, for example. In one embodiment, $K_N$ may be represented as a piecewise function such as:

$$K_N = \begin{cases} K_D & \Delta x_n < 0 \\ K_D(x_s - \Delta x_n)/x_s & 0 < \Delta x_n < x_s \\ 0 & \Delta x_n > x_s \end{cases} \quad (2)$$

where $K_D$ is a maximum damping gain, $x_s$ is a predetermined minimum safe distance, and $\Delta x_n$ is the distance between distal end 211 of surgical tool 210 and spinal cord 103 measured by neural monitor 280. $K_D$ may be a predetermined constant value that may be selected to optimize the performance of CAS system 200. Safe distance $x_s$ may be determined based on, e.g., input from the surgeon. In certain embodiments, safe distance $x_s$ may be determined based on the accuracy of neural monitor 280. For example, if neural monitor 280 is capable of accurately determining a distance between distal end 211 and spinal cord 103 within y millimeters, then $x_s$ may be determined to be a value equal to (3*y) millimeters.

In another embodiment, $K_N$ may be defined in accordance with the following equation:

$$K_N = \begin{cases} K_D & \Delta x_n < x_f \\ K_D(x_s - \Delta x_n)/(x_s - x_f) & x_f < \Delta x_n < x_s \\ 0 & \Delta x_n > x_s \end{cases} \quad (3)$$

In equation (3), a threshold $x_f$ is defined such that $K_N$ is equal to the maximum damping gain $K_D$ when the distance $\Delta x_n$ less than $x_f$. Thus, in equation (3), the maximum damping gain may be applied when distal end 211 is less than a predetermined distance $x_f$ away from spinal cord 103, resulting in an increased impedance at distances where $\Delta x_n$ is still greater than 0. Threshold $x_f$ may likewise be determined based on, e.g., input from the surgeon or other user and/or based on the accuracy of neural monitor 280.

Equations (2) and (3) are merely exemplary equations for determining the value of $K_N$. In fact, $K_N$ may be expressed by any other equation such that $K_N$ increases as $\Delta x_n$ decreases over a particular range. For example, any number of linear and/or nonlinear functions may be used to represent an increase in impedance proportional to a decrease in distance between distal end 211 of surgical tool 210 and spinal cord 103. Moreover, while the embodiment discussed above calculates a virtual damping torque, those skilled in the art will appreciate that any combination of stiffness, inertia, and/or damping forces and torques may be introduced to CAS system 200 based on the distance between surgical tool 210 and spinal cord 103, as measured by neural monitor 280.

In exemplary embodiments of FIG. 5, torque $\tau_d$, generated based on the virtual haptic geometry, may be combined with a neural monitor torque $\tau_n$ generated based on a distance between surgical tool 210 and a portion of the patient's anatomy, measured by, e.g., neural monitor 280. For example, returning to FIG. 5, processor 231 may add together $\tau_n$ and $\tau_d$ to produce $\tau_c$ (block 540), a total torque value to be provided as a haptic feedback command to the force system of robotic arm 204 (block 550). Block 550 in FIG. 5 may represent the robotic dynamics of the physical system of robotic arm 204. Thus, the haptic feedback command $\tau_c$ may be provided to robotic arm 204, and one or more sensors at robotic arm 204 or elsewhere may feed back information regarding the orientation and movement of robotic arm 204. For example, as shown in FIG. 5, the joint angular velocity $q_p$ of robotic arm 204 and the actual position x of surgical tool 210 may be fed back to blocks 560 and 510, respectively.

Figure 6:
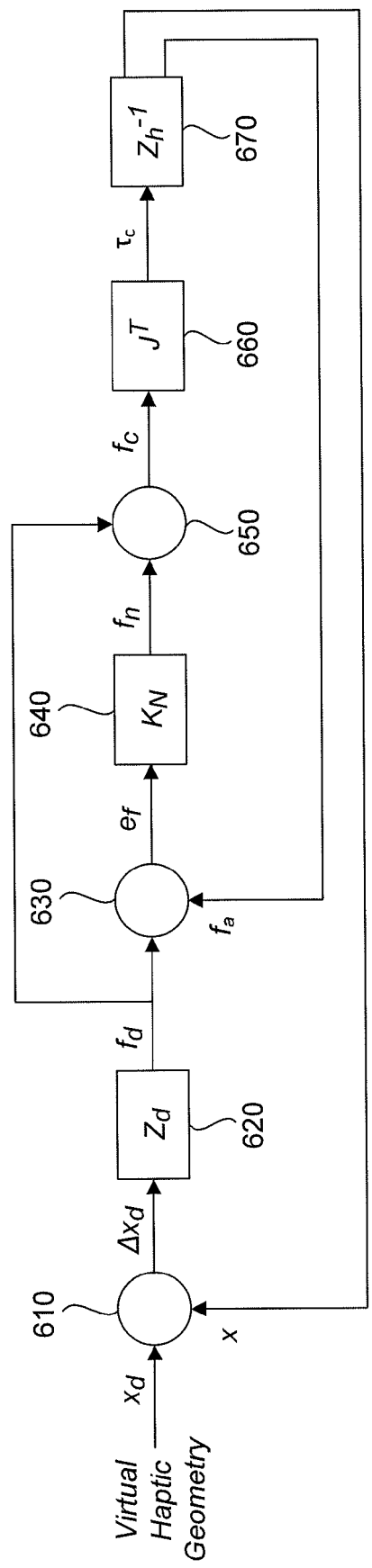
FIG. 6 is another block diagram of another exemplary control system which may be employed by the CAS system illustrated in FIG. 2.

FIG. 6 shows a system control diagram in accordance with another exemplary embodiment. In FIG. 6, processor 231 may control robotic arm 204 by means of impedance control with force feedback. That is, processor 231 may generate a dynamic impedance in robotic arm 204 by altering a contribution of a force feedback gain being applied to robotic arm 204. For example, processor 231 may alter the contribution of force feedback gain based on the distance between surgical tool 210 and spinal cord 103, as measured by neural monitor 280. The system control diagram of FIG. 6 may be used, for example, in combination with a robotic arm that exhibits high natural stiffness, damping, and/or inertia and thus may be difficult to move in its natural state. This natural impedance may be based, for example, on a transmission in robotic arm 204 having a high gear ratio. Thus, in the embodiment of FIG. 6, processor 231 may reduce an amount of force feedback gain being applied to robotic arm 204 as distal end 211 moves closer to spinal cord 103 so that the impedance of robotic arm 204 increases as distal end 211 moves closer to spinal cord 103.

For example, in FIG. 6, processor 231 may receive a desired position $x_d$ and an actual position x of surgical tool 210, similar to the embodiment of FIG. 5. Processor 231 may also calculate a difference $\Delta x_d$ between the desired position and the actual position of surgical tool 210 (block 610), and may then calculate a haptic object force $f_d$ based on difference $\Delta x_d$ (block 620). For example, processor 231 may calculate $f_d$ by multiplying difference $\Delta x_d$ by a haptic object impedance value $Z_d$. In certain embodiments, haptic object impedance value $Z_d$ may be a fixed value for the haptic object to which it corresponds. For example, haptic object impedance value $Z_d$ may be 3,000 N/m for a particular haptic object. In other embodiments, discussed in greater detail below, haptic object impedance value $Z_d$ may be variable.

Moreover, in one embodiment, haptic object impedance value $Z_d$ may include several components, such as an inertia component M, a damping component B, and a stiffness component K. In this embodiment, processor 231 may also determine a first derivative and/or a second derivative of the difference values $\Delta x_d$, and may calculate haptic object force $f_d$ based on the impedance components M, B, and/or K as well as $\Delta x_d$ and its first and/or second derivatives. For example, processor 231 may determine $f_d$ in accordance with equation (1), discussed above. In one embodiment, M may be equal to zero, such that $f_d$ is determined based on a damping component B and a stiffness component K.

Processor 231 may determine a difference between haptic object force $f_d$ and applied force $f_a$ to determine a force error value $e_f$ (block 630). Applied force $f_a$ may represent an amount of force being applied to robotic arm 204 by a user (e.g., a surgeon). For example, as discussed above with regard to FIG. 3, robotic arm 204 may include one or more force sensors 270 to measure an amount of force being applied to it by the user. Robotic arm 204 may then send electronic signals indicative of the applied force values $f_a$ to processor 231.

Processor 231 may then generate a modified force feedback value $f_n$ such that $f_n = e_f * K_N$, where $K_N$ represents the neural monitor gain (block 640). Neural monitor gain $K_N$ may be variable based on the distance between surgical tool 210 and a portion of the patient's anatomy, such as spinal cord 103, as measured by neural monitor 280, for example. For example, in one embodiment, $K_N$ may be represented as a piecewise function such as:

$$K_N = \begin{cases} 0 & \Delta x_n < 0 \\ (K_F \Delta x_n)/x_s & 0 < \Delta x_n < x_s \\ K_F & \Delta x_n > x_s \end{cases} \quad (4)$$

where $K_F$ is a maximum force feedback gain, $x_s$ is a predetermined minimum safe distance, and $\Delta x_n$ is the distance between distal end 211 of surgical tool 210 and spinal cord 103. $K_F$ may be a predetermined constant value that may be selected to optimize the performance of CAS system 200. Safe distance $x_s$ may be determined based on, e.g., input from the surgeon. In certain embodiments, $x_s$ may be determined based on the accuracy of neural monitor 280. For example, if neural monitor 280 can accurately determine a distance between distal end 211 and spinal cord 103 within y millimeters, then $x_s$ may be determined to be a value equal to (3*y) millimeters.

Equation (3) is an exemplary equation for determining the value of $K_N$. In fact, $K_N$ may be expressed by any other equation such that $K_N$ decreases as $\Delta x_n$ decreases over a particular range for embodiments associated with FIG. 6. By decreasing the neural monitor gain $K_N$ for a corresponding decrease in the distance $\Delta x_n$ between distal end 211 and spinal cord 103, processor 231 may reduce the force feedback of robotic arm 204 to zero (or a near-zero value) based on the proximity of surgical tool 210 to the nervous system. If, as discussed above, robotic arm 204 exhibits high natural impedance, then reducing the force feedback will make robotic arm 204 (e.g., articulated arm 206) increasingly difficult to move as distal end 211 moves closer to spinal cord 103.

Moreover, any number of linear and/or nonlinear functions may represent $K_N$ so as to generate an increased impedance proportional to a decrease in distance spinal cord 103. Moreover, in another embodiment, equation (4) may be modified to include a threshold $x_f$ defined such that the force feedback gain is zero when the distance between distal end 211 and spinal cord 103 is within the threshold distance $x_f$. For example, $K_N$ may be represented as:

$$K_N = \begin{cases} 0 & \Delta x_n < x_f \\ K_F(\Delta x_n - x_f)/(x_s - x_f) & 0 < \Delta x_n < x_s \\ K_F & \Delta x_n > x_s \end{cases} \quad (5)$$

Still further, equation (5) may be modified to be a non-linear function of the distance between distal end 211 and spinal cord 103 such that:

$$K_N = \begin{cases} 0 & \Delta x_n < x_f \\ K_F((\Delta x_n - x_f)/(x_s - x_f))^b & 0 < \Delta x_n < x_s \\ K_F & \Delta x_n > x_s \end{cases} \quad (6)$$

where b is a scalar coefficient greater than 1. Those skilled in the art will appreciate that other equations may be used to represent $K_N$, consistent with the spirit and scope of the disclosed embodiments.

After calculating the modified force feedback value $f_n$ as described above, processor 231 may generate a combined force value $f_c$ by adding a feedforward value of $f_d$ and the modified force feedback value $f_n$ (block 650). Processor 231 may then utilize the Jacobian transpose to determine a haptic feedback command $\tau_c$ with a torque value corresponding to the combined force value $f_c$ (block 660).

Processor 231 may provide haptic feedback command $\tau_c$ to the force system of robotic arm 204 (block 670). For example, block 670 in FIG. 6 may represent the robotic dynamics of the physical system of robotic arm 204. Thus, the haptic feedback command $\tau_c$ may be provided to robotic arm 204, and one or more sensors at robotic arm 204 or elsewhere may feed back information regarding the orientation and movement of robotic arm 204, as well as forces being applied thereto. For example, as shown in FIG. 6, the actual position x of surgical tool 210 may be fed back to block 610 and, as discussed above, a force $f_a$ being applied by the surgeon to robotic arm 204 may be fed back to block 630.

Figure 7:
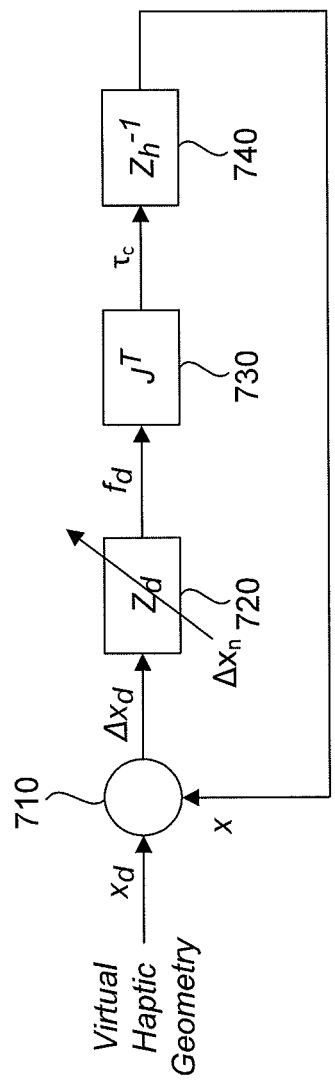
FIG. 7 is another block diagram of yet another exemplary control system which may be employed by the CAS system illustrated in FIG. 2.

FIG. 7 shows a system control diagram in accordance with yet another exemplary embodiment. In FIG. 7, processor 231 may control robotic arm 204 by direct modification of haptic object impedance value $Z_d$. For example, as discussed above with regard to FIGS. 5 and 6, haptic object impedance value $Z_d$ may be a fixed value for the haptic object to which it corresponds. However, in FIG. 7, processor 231 may dynamically alter haptic object impedance value $Z_d$ based on, e.g., the distance between distal end 211 of surgical tool 210 and a portion of the patient's anatomy, such as spinal cord 103, as measured by neural monitor 280.

For example, in FIG. 7, processor 231 may receive a desired position $x_d$ and an actual position x of surgical tool 210, as discussed above with respect to FIG. 5. Processor 231 may also calculate a difference $\Delta x_d$ between the desired position and the actual position of surgical tool 210 (block 710), and may then calculate a force, $f_d$, based on difference $\Delta x_d$ (block 720). For example, processor 231 may calculate $f_d$ in accordance with equation (1), discussed above. However, in embodiments associated with FIG. 7, one or more of an inertia component M, a damping component B, and a stiffness component K of impedance value $Z_d$, as shown in equation (1), may be variable functions of $\Delta x_n$. In certain embodiments, one or more of M, B, or K may be defined as a piecewise linear or non-linear function of $\Delta x_n$. For example, damping component B may be defined as:

$$B = \begin{cases} B_{max} & \Delta x_n < x_f \\ B_{max}(\Delta x_n - x_s)/(x_f - x_s) & x_f < \Delta x_n < x_s \\ 0 & \Delta x_n > x_s \end{cases} \quad (7)$$

where $B_{max}$ is a maximum damping component value, $x_s$ is a predetermined minimum safe distance, $x_f$ is a threshold value, and $\Delta x_n$ is the distance between distal end 211 of surgical tool 210 and spinal cord 103. $B_{max}$ may be a predetermined constant value that may be selected to optimize the performance of CAS system 200. Safe distance $x_s$ and threshold $x_f$ may be determined based on, e.g., input from the surgeon or other user or based on the accuracy of neural monitor 280. While equation (7) defines B as having a value of 0 for $\Delta x_e > x_s$, B may also be defined to be some non-zero value $B_{min}$ for this range. For example, $B_{min}$ may represent a minimum damping present in robotic arm 204 and may be selected in a manner that optimizes the performance of CAS system 200. Moreover, equation (7) is merely an exemplary equation for representing B, and those skilled in the art will appreciate that B may be represented by other equations, such as a non-linear piecewise equation or any other linear or non-linear equations consistent with disclosed embodiments. Also, while stiffness component B is used in the example above, inertia component M and stiffness component K may also be represented by equations similar to those described above with respect to damping component B. By varying one or more of M, B, or K as a function of $\Delta x_n$, processor 231 may calculate a variable haptic object impedance value $Z_d$ such that $Z_d$ also varies based on $\Delta x_n$, the distance between surgical tool 210 and a portion of the patient's anatomy, such as spinal cord 103, as measured by neural monitor 280.

After calculating force $f_d$, processor 231 may calculate a torque to be applied to robotic arm 204 as haptic feedback command $\tau_c$ (block 730). Thus, at block 730, processor 231 may utilize the Jacobian transpose to determine a torque $\tau_c$ with a value corresponding to the desired force value $f_d$.

Processor 231 may then provide haptic feedback command $\tau_c$ to the force system of robotic arm 204 to control one or more actuators at corresponding joints of robotic arm 204 (block 740). For example, block 740 of FIG. 7 may represent the robotic dynamics of the physical system of robotic arm 204. Thus, haptic feedback command $\tau_c$ may be provided to robotic arm 204, and one or more sensors at robotic arm 204 or elsewhere may feed back information regarding the orientation and movement of robotic arm 204. For example, as shown in FIG. 7, the actual position x of surgical tool 210 may be fed back to block 710.

Figure 8:
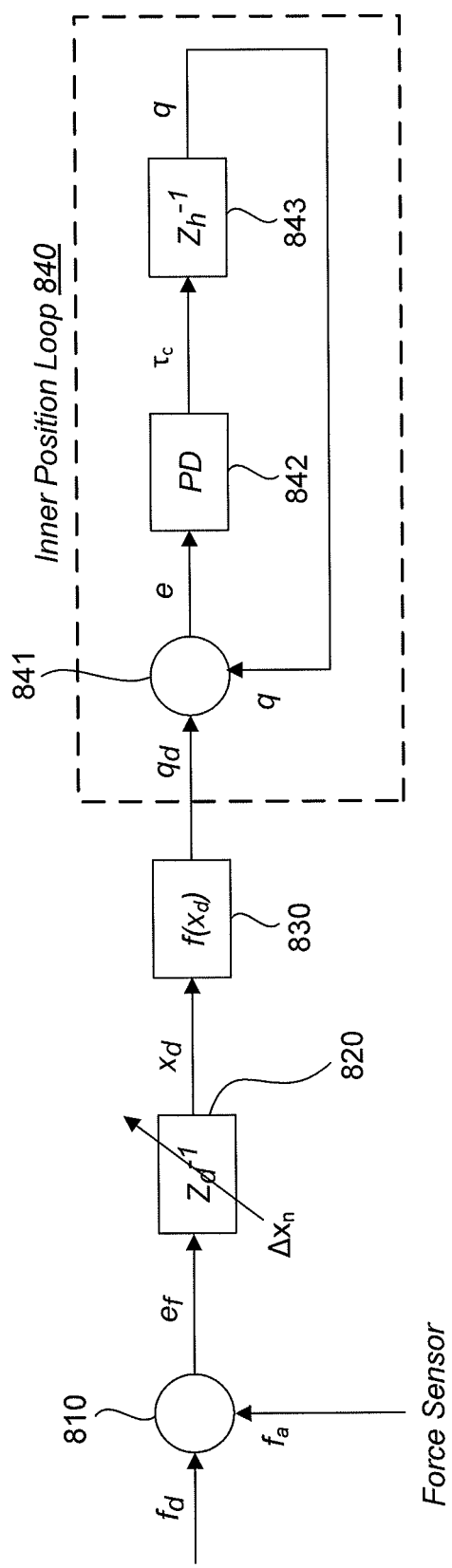
FIG. 8 is another block diagram of yet another exemplary control system which may be employed by the CAS system illustrated in FIG. 2.

FIG. 8 shows a system control diagram in accordance with yet another exemplary embodiment. In FIG. 8, processor 231 may control robotic atm 204 by direct modification of a haptic object admittance value $Z_d^{-1}$. For example, the control system illustrated in FIG. 8 may be an admittance-based control system, such that processor 231 receives measurements of forces being applied to robotic arm 204, generates a desired position of robotic arm 204 based on the measured forces, and then sends commands to drive robotic arm 204 to the desired position.

For example, in FIG. 8 processor 231 may receive a desired force value $f_d$ and an applied force value $f_a$. Desired force value $f_d$ represents the desired force at an end effector of robotic arm 204 (e.g., surgical tool 210) and may be a constant value or may be variable. In one embodiment, robotic arm 204, at times, may be operated in a zero-gravity mode where $f_d=0$. Applied force $f_a$ represents a force being applied to surgical tool 210 by a user, e.g., a surgeon. For example, as discussed above, CAS system 200 may include one or more force sensors 270 for measuring applied force $f_a$. Force sensors 270 may send a signal to processor 231 indicative of applied force $f_a$. Processor 231 may determine a force error value $e_f$ such that $e_f = f_d - f_a$ (block 810).

Processor 231 may determine a desired position $x_d$ of surgical tool 210 based on the determined force error value $e_f$ (block 820). Desired position $x_d$ may include a point or set of points in three-dimensional space that represent the desired position of surgical tool 210. Processor 231 may determine desired position $x_d$ based on a haptic object admittance $Z_d^{-1}$. Haptic object admittance value $Z_d^{-1}$ may be defined such that $x_d$ may be determined in accordance with the following equation:

$$e_f = M(\ddot{x}_d) + B(\dot{x}_d) + K(x_d). \tag{8}$$

where M, B, and K are inertia, damping, and stiffness components, respectively. In embodiments associated with FIG. 8, one or more of M, B, and K may be variable functions of $\Delta x_e$, such that the haptic object admittance $Z_d^{-1}$ is also variable based on $\Delta x_e$, the distance between distal end 211 of surgical tool 210 and spinal cord 103, as measured by neural monitor 103. In certain embodiments, one or more of M, B, or K may be defined as a piecewise linear or non-linear function of $\Delta x_e$. For example, M, B, and/or K may be defined as discussed above with respect to FIG. 7. Processor 231 may then solve equation (8) to determine desired position $x_d$ for a given force error $e_f$ using, e.g., numerical integration.

Processor 231 may use desired position $x_d$ to determine one or more desired joint angular positions $q_d$ for the corresponding one or more joints of robotic arm 204 (block 830). For example, processor 231 may use one or more coordinate transform functions and/or inverse kinematics functions, $f(x_d)$, to translate the desired position $x_d$ in three-dimensional space to one or more joint angular positions $q_d$, e.g., in angular space, that result in surgical tool 210 being positioned in desired position $x_d$.

Processor 231 may send commands to one or more actuators in robotic arm 204 such that the actual joint angular positions q of robotic arm 204 (e.g., of articulated arm 206) equal their corresponding desired joint angular positions $q_d$. Processor 231 may generate these commands using a feedback control loop such as inner position loop 840. For example, processor 231 may compare desired joint angular positions $q_d$ to actual joint angular positions q to determine a joint angular position error $e = q_d - q$ (block 841). Actual joint angular positions q may be measured by one or more sensors at robotic arm 204.

Processor 231 may determine a torque value for a haptic feedback command $\tau_c$ using, e.g., a proportional plus derivative controller (block 842). Processor 231 may then provide haptic feedback command $\tau_c$ to the force system of robotic arm 204 to control one or more actuators at corresponding joints of robotic arm 204 (block 843). For example, block 843 of FIG. 7 may represent the robotic dynamics of the physical system of robotic arm 204. Thus, processor 231 may provide haptic feedback command $\tau_c$ to robotic arm 204, and one or more sensors at robotic arm 204 or elsewhere may feed back information regarding the orientation and movement of robotic arm 204. For example, as shown in FIG. 8, the actual joint angular positions q of robotic arm 204 may be fed back to block 710.

Figure 9:
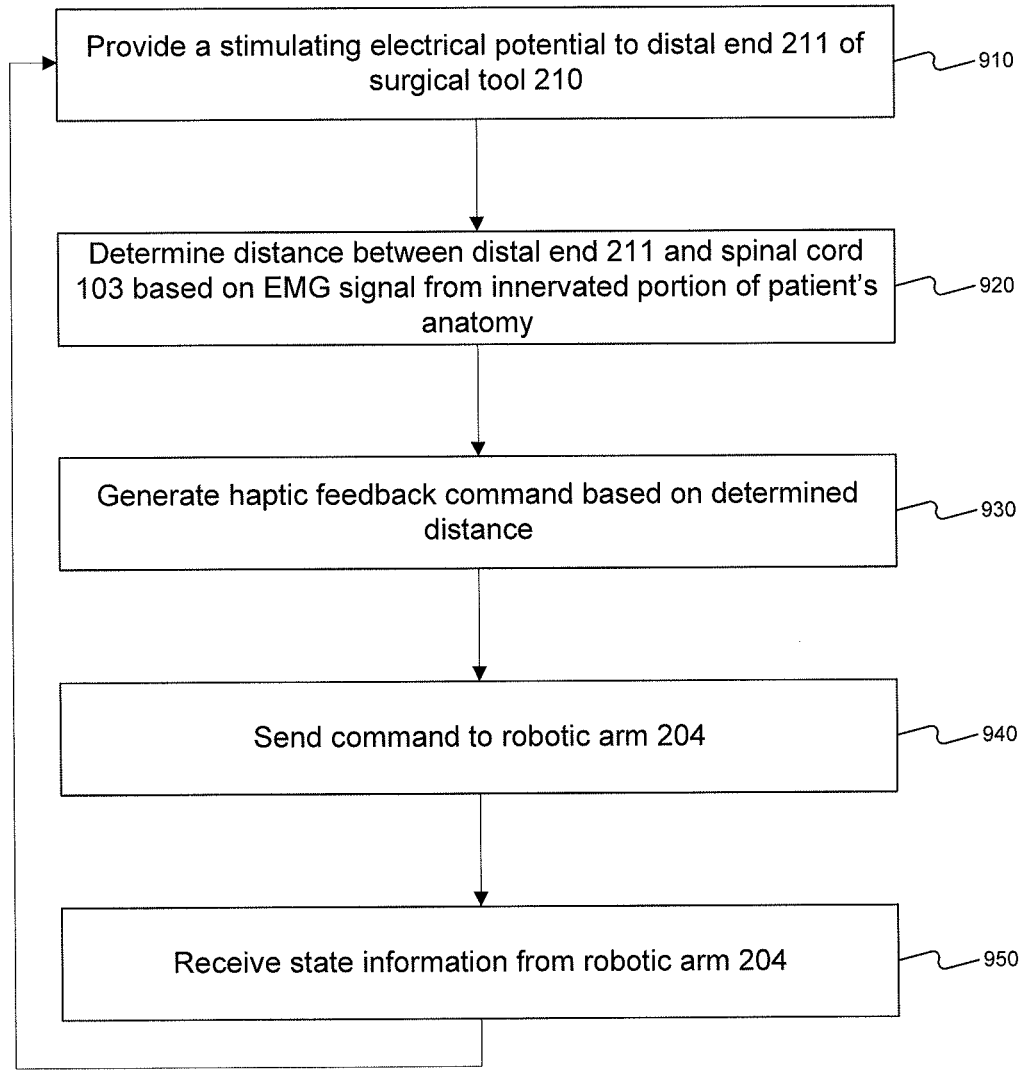
FIG. 9 is a flowchart of an exemplary method for dynamically generating haptic feedback commands consistent with disclosed embodiments.

FIG. 9 illustrates a flowchart of an exemplary neural monitor-based dynamic haptics process that may be performed by, e.g., CAS system 200 or one or more of its components. According to the exemplary process of FIG. 9, CAS system 200 may provide a stimulating electrical potential to distal end 211 of surgical tool 210 (step 910). The stimulating potential may be generated, e.g., by neural monitor 280, as discussed above.

CAS system 200 may also determine a distance between distal end 211 and spinal cord 103 based on an EMG signal received from an innervated portion of the patient's anatomy (step 920). For example, the stimulating potential applied in step 910 may cause nerves in spinal cord 103 to innervate one or more muscles or other groups of tissue near or around spinal cord 103. One or more sensors associated with neural monitor 280 may detect EMG signals generated by the muscles or other tissue innervated by spinal cord 103. Based on an intensity of the EMG signal received, neural monitor 280 may determine a distance between distal end 211 and spinal cord 103.

Based on the determined distance, CAS system 200 may generate haptic feedback commands used to control robotic arm 204 (step 930). That is, CAS system 200 may dynamically alter the haptic feedback commands being sent to robotic arm 204 based on a determined distance between distal end 211 and spinal cord 103. For example, CAS system 200 may dynamically vary the degree to which robotic arm 204 resists movement based on the signals received from neural monitor 280, e.g., according to one or more of the embodiments discussed above with regard to FIGS. 5-8.

Once the command is generated, CAS system 200 may send the command to robotic arm 204 (step 940). For example, CAS system 200 may send the command via an I/O device to the force system or the control system of robotic arm 204. Robotic arm 204 may then send corresponding commands to one or more actuators in robotic arm 204 to control movement and/or forces within robotic arm 204 based on the received haptic feedback command.

CAS system 200 may also receive state information from robotic arm 204 (step 950). For example, as discussed above, robotic arm 204 may include one or more sensors, such as applied force sensors, joint angular position sensors, joint angular velocity sensors, or any other sensors, to determine a state of robotic arm 204. Signals from one or more of these sensors may be fed back to CAS system 200. For example, in embodiments discussed above with respect to FIG. 5, position signal x and joint angular velocity signal $q_p$ are fed back to CAS system 200.

CAS system 200 may continuously repeat steps 910-950 such that CAS system 200 continuously monitors a distance between distal end 211 of surgical tool 210 and spinal cord 103, and dynamically generates and sends haptic feedback commands to robotic arm 204 based on the determined distance.

The presently disclosed systems and methods provide a solution that enables a computer-assisted surgical system to dynamically alter a degree to which a robotic arm of the system resists movement based on a distance between a surgical tool of the robotic arm and a portion of the patient's anatomy, such as a spinal cord, detected by a neural monitor. By dynamically altering the degree to which the robotic arm resists movement, systems and method consistent with disclosed embodiments may provide haptic feedback to a surgeon operating the robotic arm based on a measured proximity to the spinal cord or other nerves. As a result, the disclosed systems and methods may prevent a surgeon from unwanted interaction with or damage to the patient's spinal cord or other nerves.

Moreover, as discussed above, systems and methods consistent with the disclosed embodiments may dynamically alter a degree to which the robotic arm resists movement in several different ways. For example, exemplary systems and methods may alter the degree to which a robotic arm resists movement by generating a damping torque based on the distance measured by the neural monitor. Further, such systems and methods may alter the degree to which a robotic arm resists movement by modifying an amount of force feedback being applied to the robotic arm based on the measured distance. Still further, such systems and methods may alter the degree to which a robotic arm resists movement by directly modifying a haptic object impedance or haptic object admittance value based on the measured distance.

It will be apparent to those skilled in the art that various modifications and variations can be made to the disclosed systems and associated methods for neural monitor-based dynamic haptics. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A computer-implemented method for controlling a surgical system, the method comprising:

receiving, from a neural monitor, a signal indicative of a distance between a surgical tool connected to a robotic arm and a portion of a patient's anatomy including nervous tissue; and generating a command for altering a degree to which the robotic arm resists movement based on the signal received from the neural monitor, wherein generating the command comprises:

generating a first force value based on virtual haptic geometry associated with the patient's anatomy;

subtracting an applied force being applied to the robotic arm from the first force value to calculate a force error;

determining a neural monitor gain based on the signal received from the neural monitor;

generating a second force value proportional to the force error and the neural monitor gain; and generating the command based on a combination of the first force value and the second force value.

2. The computer-implemented method of claim 1, generating the command further comprising:

generating a first torque value based on virtual haptic geometry associated with the patient's anatomy;

generating a second torque value based on the signal received from the neural monitor; and generating the command by combining the first torque value and the second torque value.

3. The computer-implemented method of claim 2, generating the second torque value further comprising:

receiving a joint angular velocity of one or more joints of the robotic arm;

determining a second neural monitor gain based on the signal received from the neural monitor; and generating the second torque value proportional to the second neural monitor gain and the joint angular velocity of the one or more joints of the robotic arm.

4. The computer-implemented method of claim 3, wherein the second neural monitor gain is a piecewise function of the distance between the surgical tool and the portion of the patient's anatomy including nervous tissue.

5. The computer-implemented method of claim 1, generating the command further comprising:

receiving an applied force signal indicative of an applied force being applied to the robotic arm;

generating a force feedback signal based on the applied force signal and the signal received from the neural monitor; and generating the command based on the force feedback signal.

6. The computer-implemented method of claim 1, generating the command further comprising:

dynamically altering a haptic object impedance value based on the signal received from the neural monitor, the dynamically altered haptic object impedance value corresponding to virtual haptic geometry associated with the patient's anatomy; and generating the command based on the dynamically altered haptic object impedance value.

7. The computer-implemented method of claim 1, generating the command further comprising:

dynamically altering a haptic object admittance value based on the signal received from the neural monitor, the dynamically altered haptic object admittance value corresponding to virtual haptic geometry associated with the patient's anatomy; and generating the command based on the dynamically altered haptic object admittance value.

8. The computer-implemented method of claim 1, the method further comprising:
  providing an electrical potential to the surgical tool;
  measuring an electromyographic signal at another portion of the patient's anatomy innervated by the portion of the patient's anatomy including nervous tissue; and
  generating the signal indicative of the distance between the surgical tool and the portion of the patient's anatomy including nervous tissue based on the electromyographic signal.

9. The computer-implemented method of claim 1, wherein the portion of the patient's anatomy including nervous tissue is a spinal cord.

10. A computer-assisted surgery system comprising:
  a robotic arm including a surgical tool; and
  a processor communicatively connected to the robotic arm and configured to:
    receive, from a neural monitor, a signal indicative of a distance between the surgical tool and a portion of a patient's anatomy including nervous tissue; and
    generate a command for altering a degree to which the robotic arm resists movement based on the signal received from the neural monitor, wherein generating the command comprises:
      generating a first force value based on virtual haptic geometry associated with the patient's anatomy;
      subtracting an applied force being applied to the robotic arm from the first force value to calculate a force error;
      determining a neural monitor gain based on the signal received from the neural monitor;
      generating a second force value proportional to the force error and the neural monitor gain; and
      generating the command based on a combination of the first force value and the second force value; and
    send the command to the robotic arm.

11. The computer-assisted surgery system of claim 10, further comprising the neural monitor, wherein the neural monitor is configured to:
  provide an electrical potential to the surgical tool;
  measure an electromyographic signal at another portion of the patient's anatomy innervated by the portion of the patient's anatomy including nervous tissue; and
  generate the signal indicative of the distance between the surgical tool and the portion of the patient's anatomy including nervous tissue based on the electromyographic signal.

12. The computer-assisted surgery system of claim 10, the processor being further configured to:
  generate a first torque value based on virtual haptic geometry associated with the patient's anatomy;
  generate a second torque value based on the signal received from the neural monitor; and
  generate the command by combining the first torque value and the second torque value.

13. The computer-assisted surgery system of claim 12, the processor being further configured to:
  receive a joint angular velocity of one or more joints of the robotic arm;
  determine a second neural monitor gain based on the signal received from the neural monitor; and generate the second torque value proportional to the second neural monitor gain and the joint angular velocity of the one or more joints of the robotic arm.

14. The computer-assisted surgery system of claim 10, the processor being further configured to:
  receive an applied force signal indicative of an applied force being applied to the robotic arm;
  generate a force feedback signal based on the applied force signal and the signal received from the neural monitor; and
  generate the command based on the force feedback signal.

15. The computer-assisted surgery system of claim 10, the processor being further configured to:
  dynamically alter a haptic object impedance value based on the signal received from the neural monitor, the dynamically altered haptic object impedance value corresponding to virtual haptic geometry associated with the patient's anatomy; and
  generate the command based on the dynamically altered haptic object impedance value.

16. The computer-assisted surgery system of claim 10, the processor being further configured to:
  dynamically alter a haptic object admittance value based on the signal received from the neural monitor, the dynamically altered haptic object admittance value corresponding to virtual haptic geometry associated with the patient's anatomy; and
  generate the command based on the dynamically altered haptic object admittance value.

17. A computer-implemented method for controlling a surgical system, the method comprising:
  receiving, at a processor associated with a computer, a signal from a neural monitor indicative of a distance between a surgical tool connected to a robotic arm and a portion of a patient's anatomy including nervous tissue; and
  determining, by the processor, a haptic feedback command based on the signal received from the neural monitor, wherein determining a haptic feedback command comprises:
    determining a first force value based on virtual haptic geometry associated with the patient's anatomy;
    subtracting an applied force being applied to the robotic arm from the first force value to calculate a force error;
    determining a neural monitor gain based on the signal received from the neural monitor;
    determining a second force value proportional to the force error and the neural monitor gain; and
    determining the haptic feedback command based on a combination of the first force value and the second force value.

18. The computer-implemented method of claim 17, wherein the haptic feedback command dynamically alters a degree to which the robotic arm resists movement by generating a damping torque based on the neural monitor signal.

19. The computer-implemented method of claim 17, wherein the haptic feedback command dynamically alters a degree to which the robotic arm resists movement by modifying an amount of force feedback being applied to the robotic arm based on the neural monitor signal.

20. The computer-implemented method of claim 17, wherein the haptic feedback command dynamically alters a degree to which the robotic arm resists movement by altering a haptic object impedance value based on the neural monitor signal.

21. The computer-implemented method of claim 17, wherein the haptic feedback command dynamically alters a degree to which the robotic arm resists movement by altering a haptic object admittance value based on the neural monitor signal.

* * * * *